(12) United States Patent
Fernandez Martinez et al.

(10) Patent No.: US 8,404,476 B2
(45) Date of Patent: Mar. 26, 2013

(54) **PURE CULTURE OF STRAIN AH2 OF THE *BACILLUS VELEZENSIS* SPECIES AND A PRODUCT FOR THE BIOLOGICAL CONTROL OF PHYTOPATHOGENIC FUNGI**

(75) Inventors: Ana Isabel Fernandez Martinez, Murcia (ES); Mario Jorge Villaverde Fernandez, Murcia (ES); Juan Antonio Casanova Roca, Santomera (ES); Jorge Malo Lopez-Roman, Murcia (ES); Jose Antonio Nicolas Martinez, Espinardo (ES); Isidro Blanca Picó, Torreagüera (ES)

(73) Assignee: Probelte, S.A., Espinardo (ES)

( * ) Notice: Subject to any disclaimer, the term of this patent is extended or adjusted under 35 U.S.C. 154(b) by 631 days.

(21) Appl. No.: 12/531,933

(22) PCT Filed: Feb. 27, 2008

(86) PCT No.: PCT/ES2008/000109
§ 371 (c)(1),
(2), (4) Date: Mar. 15, 2010

(87) PCT Pub. No.: WO2008/113873
PCT Pub. Date: Sep. 25, 2008

(65) Prior Publication Data
US 2010/0179060 A1    Jul. 15, 2010

(30) Foreign Application Priority Data
Mar. 19, 2007    (ES) .................................. 200700711

(51) Int. Cl.
*C12N 1/20* (2006.01)
*A01N 63/00* (2006.01)
(52) U.S. Cl. .................. 435/252.5; 504/117; 424/93.46
(58) Field of Classification Search ........................ None
See application file for complete search history.

(56) References Cited

U.S. PATENT DOCUMENTS

| | | |
|---|---|---|
| 6,077,506 A | 6/2000 | Marrone et al. |
| 6,306,386 B1 | 10/2001 | Cole et al. |
| 6,890,530 B2 | 5/2005 | Hermosa Prieto et al. |
| 7,087,424 B1 | 8/2006 | Nayudu et al. |
| 7,118,739 B2 | 10/2006 | da Luz |
| 2003/0211081 A1 | 11/2003 | da Luz |
| 2004/0176249 A1 | 9/2004 | Prieto et al. |
| 2005/0096225 A1* | 5/2005 | Johnson ........................ 504/100 |

FOREIGN PATENT DOCUMENTS

| | | |
|---|---|---|
| EP | 1 647 188 A2 | 4/2006 |
| ES | 2 234 417 | 6/2005 |
| WO | WO 2004/024865 A2 | 3/2004 |
| WO | WO 2005/059112 * | 6/2005 |

OTHER PUBLICATIONS

Uniprot (http://www.uniprot.org/taxonomy/1390). (accessed Jul. 25, 2012).*
International Search Report for PCT International Application No. PCT/ES2008/000109 mailed Aug. 1, 2008.
Ruiz-García et al., "*Bacillus velezensis* sp. nov., a surfactant-producing bacterium isolated from the river Vélez in Málaga, southern Spain," Intl. Journal of Systematic and Evolutionary Microbiology (2005), 55, 191-195.
Wang et al., "*Bacillus velezensis* is a later heterotypic synonym of *Bacillus amyloliquefaciens*," Intl. Journal of Systematic and Evolutionary Microbiology (2008), 58, 671-675.

* cited by examiner

*Primary Examiner* — Irene Marx
(74) *Attorney, Agent, or Firm* — RatnerPrestia

(57) ABSTRACT

The invention relates to a new fungicide product for the biological control of phytopathogenic fungi, which contains a new isolate of *Bacillus velezensis* strain AH2, deposited in the Spanish Type Culture Collection (CECT) as CECT-7221, which has a high antagonist activity against this type of pathogen, as well as the property of stimulating plant growth by different mechanisms. The invention also relates to a liquid formulation which has good stability at ambient temperature and is effective in the treatment of diseases caused by phytopathogenic fungi and for the stimulation of plant growth.

9 Claims, 2 Drawing Sheets

*Botrytis* sp.

*Fusarium* sp.

*Pythium* sp.

*Phytophthora* sp.

*Rhizoctonia* sp.

*Botryosphaeria* sp.

Legend: PFV: Green fresh weight, PFR: Root fresh weight, PFT: Total fresh weight

PURE CULTURE OF STRAIN AH2 OF THE *BACILLUS VELEZENSIS* SPECIES AND A PRODUCT FOR THE BIOLOGICAL CONTROL OF PHYTOPATHOGENIC FUNGI

This application is a U.S. National Phase Application of PCT International Application No. PCT/ES2008/000109, filed Feb. 27, 2008.

FIELD OF THE INVENTION

The present invention is a product for the biological control of phytopathogenic fungi, formed by viable cells of a new isolate of *Bacillus velezensis* (Ruiz-García et al., 2005) strain AH2, having a high antifungal activity, particularly against different phytopathogenic fungi, as well as a good capacity to stimulate plant growth by means of different mechanisms. The product has been formulated from a fermented broth, obtained by means of a stirred submerged culture, which is used directly in the formulation. This formulation maintains a high activity for at least six months at ambient temperature. The *Bacillus velezensis* strain AH2 used in obtaining the formulation is furthermore an object of the present invention.

STATE OF THE ART

The need and importance of developing and amplifying Integrated Production and Organic Agriculture processes, as an alternative to the indiscriminate use of chemical products in agriculture, in order to reduce the harmful effects of the latter have long been acknowledged. The use of biopreparations from microorganisms for the biological control of pests and diseases, as well as for the fertilization of crops of commercial interest, is one of the most promising alternatives within this context. Furthermore, these biopreparations play an important role in sustainable agriculture models due to the possibility of being produced from renewable resources (Alfieri, 1997).

The main advantage of this route is that, since it is based on natural mechanisms, it is an environmentally friendly, non-polluting ecological alternative which considerably reduces the risks of the pathogens acquiring resistance. Also, since they are selective in their mode of action, it is generally is less likely that they harm other beneficial organisms and in many cases they benefit the ecosystem and stimulate plant growth, making agricultural production more sustainable, while at the same time the effects on human health are minimal or nil. Virtually all pests and diseases are affected to some extent by antagonist organisms. In many cases these biological entities represent the most important factor in regulating populations of pathogenic organisms in nature.

One of the most important groups among the organisms causing plant diseases are phytopathogenic fungi, including species of the *Botrytis, Pythium, Rhizoctonia, Alternaria, Fusarium, Phytophthora, Thielaviopsis* and *Botryosphaeria* genera among many others, which can survive for many years in soil.

In the search for agents for biological control which can have a commercial interest, a series of factors must be taken into account which, studied together, may lead to a successful result. The biological entities to be used either independently or in mixed inocula, the specific biological activity, the mechanisms of action against the pathogen, the production system used, as well as the type of formulation and its stability (Warrior, 2000) could be mentioned among them.

Several mechanisms have been described to explain the phenomenon of biological control of these pathogens, such as parasitism, cross-protection, antibiosis, competition and induction of resistance, among others (Shoda, 2000, Walsh et al. 2001).

One of the most studied ecological niches has been the rhizosphere, due to the relationships established herein between plants and other organisms (Warrior, 2000). The microorganisms of the rhizosphere have being studied since the 1980s as possible substitutes of chemical pesticides to control a wide range of diseases. Due to their abundant distribution in soil, their capacity to colonize the roots of plants, and to produce a large variety of beneficial compounds, as well as antagonists of a large number of pathogens, these organisms are highly suitable for the biological control of pests and diseases. (Anjaiah et al., 1998; Hill et al., 1994; Maurhofer et al., 1991; Rodriguez, and Pfender. 1997; Ross et al., 2000 and Thomashow et al., 1997).

Among the microbial groups of the rhizosphere, which have been extensively studied as agents for the biological control of pests and diseases caused by the microorganisms, is the group formed by fungi. It has been used successfully in the control of pathogenic fungi belonging to the *Botrytis, Fusarium, Pythium, Phytophthora, Rhizoctonia, Sclerotinia, Penicillium,* and *Macrophomina* genera and others (Whipps and Lumsden, 2001, McQuilken et al., 2001, Jones and Whipps, 2002, among others). Given its varied metabolism, this microbial group is capable of producing a large variety of substances useful for biological control. For these reasons, the number of strains and products based on fungi for this purpose is increasingly larger and more varied (Cook et al., 1996, Whipps, 1997, Fravel et al., 1998, EPA USA 2006. U.S. Pat. No. 6,306,386 and U.S. Pat. No. 6,890,530 among others). The mechanisms by means of which the biological control of the diseases is exerted are complex and it is known that it can be the result of the addition or synergy between several of them. Among these is the competition for nutrients and space, the capacity to produce substances preventing the germination of the spore (fungistasis) or to produce cell death (antibiosis) and the modification of the rhizosphere by acidifying the soil, which prevents the proliferation of the pathogen. Biocontrol can also be a result of a direct interaction between the pathogen and the biocontrol agent (parasitism), by means of hydrolytic enzymes such as chitinases and glucanases, or the joint action of the latter and toxic metabolites (Benitez, et al., 2004).

The use of the plant growth-promoting rhizobacteria (PGPR) for the biological control of pests and diseases has been also extensively studied. The main particularity of this type of agents is that in addition to their protective effect, they have a high capacity to colonize the roots of plants and a high plant growth-stimulating power, which adds a general improvement of the health of the crops to the protective effect and thus, the plant is also more resistant to the attack of pathogens. This group of agents has been used in diseases caused by phytopathogenic fungi belonging to the *Rhizoctonia, Fusarium, Pythium, Thielaviopsis, Penicillium, Alternaria* and *Botrytis* genera among others (Emmert and Handelsman, 1999, Ligon, et al., 2000, Cavaglieri, et al., 2004 and Roberts, et al., 2005, U.S. Pat. No. 7,118,739, among others).

The *Pseudomonas* genus has been the object of a number of studies over the years as it is one of the most active and dominant agents in the rhizosphere (Geels and Schippers, 1983, de Freitas and Germida 1991, de la Cruz et al., 1992, Ligon, et al., 2000, U.S. Pat. No. 7,087,424). Members of the genus produce different antibiotics which are closely related to the reduction and suppression of plant diseases. Another factor that plays an important role in this phenomenon is the production of siderophores, which furthermore contributes to plant growth by the iron supply route. This ability is highly extended in members of the *Pseudomonas* genus. However, the incapacity of the genus to produce structures of resistance during its growth limits to some extent the stability and effectiveness of the biopreparations obtained with strains of this genus.

The *Bacillus* genus has also been extensively studied as it has great potentialities in this sense. Its has as main characteristics the fact of being virtually omnipresent in all types of soils, to which it adds a high heat tolerance, a fast growth in liquid media and the formation of spores of resistance which allows it to survive for long time periods. All this confers to the strains of the genus a great potential as biocontrol agents. The United States Environmental Protection Agency (EPA) has registered more than ten strains of different species of this genus as biopesticides and particularly biofungicides (EPA 2006). The main mechanisms associated to the biocontrol of phytopathogenic fungi by means of strains of this genus, also include the production of antibiotics, siderophores, surfactants and hydrolytic enzymes such as chitinases among others (Utkhede, 1984, Acea et al., 1988, Stanghellini and Miller 1996, Shoda 2000, Banat et al., 2000, Zhang, et al., 2001, Ruiz-Garcia et al., 2005, U.S. Pat. No. 7,087,424 and EP1647188).

Other bacterial genera have also been studied as agents for biocontrol, the *Enterobacter, Alcaligenes, Stenotrophomonas* and *Streptomyces* genera (McClure, et al., 1998, Brewster et al., 1997, Sabaratnam and Traquair, 2002, Cavaglieri et al., 2004 and others) are among them.

The physical form of a biopreparation product is also a very important factor which must be taken into account. What is sought is that the microorganisms remain viable in inactive state or metabolically active (Fernández, 1995). This latter is one of the most important problems of Agricultural Biotechnology, since not only must the microbial cells remain viable for long time periods, but they must be capable of surviving in the environment and performing the function for which they were intended.

When referring to sporogenic microorganisms, there is generally a greater flexibility in relation to the formulation, since these organisms can survive for long time periods, being capable of germinating and multiplying once the favorable conditions are reestablished. Cell immobilization techniques offer a series of advantages with respect to free cells which make them very attractive for their practical application (Fernández, 1995, Vassileva et al., 1998a and 1998b, among others) and very particularly for environmental biotechnology. The use of immobilized cells can enhance the effects of the microorganisms without creating contamination problems, giving rise to very active and novel products (Bellota et al., 1994, Núñez, 1998, Fonseca, 1998, Spanish Pat. ES2234417).

SUMMARY OF THE INVENTION

The object of the present invention is a product for the biological control of phytopathogenic fungi, formed by viable cells of a new isolate of *Bacillus velezensis* (Ruiz-Garcia et al., 2005) strain AH2. Said strain was isolated from soils of the Region of Murcia. The main characteristic of this isolate is that it has a high antifungal activity against different agents causing diseases of crops of economical interest, such as fungi of the *Botrytis, Pythium, Rhizoctonia, Alternaria, Fusarium, Phytophthora, Thielaviopsis* and *Botryosphaeria* genera, among others. In addition, it has the capacity to stimulate plant growth by different mechanisms. Said microorganism has been deposited in the Spanish Type Culture Collection (CECT) which has assigned the accession number CECT-7221 thereto. The strain was identified by the authors and the identification in the CECT was furthermore requested. The species identification o in the CECT was carried out by means of direct PCR amplification of the 16S rRNA gene, partial sequencing thereof (with readings in both directions) and analysis of the sequences, finally concluding that it is *Bacillus velezensis*. The product for the biological control of phytopathogenic fungi and the stimulation of plant growth consists of a liquid formulation containing viable spores of the culture as the main active ingredient.

The microorganism *Bacillus velezensis* strain AH2 CECT-7221, as well as its mutants, are likewise object of this invention. It was obtained by means of a process combining the isolation in Nutrient Agar medium (Oxoid), after the elimination of vegetative cells, and the selection through its antagonist capacity against different phytopathogenic fungi, taking into account furthermore the capacity to stimulate the plant growth (Fernandez 2004). The capacity to inhibit fungal growth was determined in in vitro bioassays in Potato Dextrose Agar (PDA) medium (Oxoid). The strain AH2 was selected, by means of these bioassays, from all the tested isolates due to its high capacity to inhibit the growth of different phytopathogenic fungi, such as species of the *Botrytis, Pythium, Rhizoctonia, Alternaria, Fusarium, Phytophthora, Thielaviopsis* and *Botryosphaeria* genera. The plant growth-stimulating power was verified by means of laboratory bioassays, according to the methods described by Bashan et al., 1986, Fernandez 1995 and Bashan 1998. Its capacity to stimulate plant growth was then verified by means of greenhouse bioassays (Villaverde et al. 2004). In addition, it was verified that it is capable of solubilizing phosphates, of producing indole-3-acetic acid and other plant growth-promoting substances, as well as siderophores. The presence of the enzyme 1-aminocyclopropane-1-carboxylate deaminase was also determined through the growth in media with 1-aminocyclopropane-1-carboxylic acid (ACC) as a sole nitrogen source. All these activities corroborate its capacity to stimulate plant growth. Villaverde et al., 2004).

Likewise, the process of obtaining the product for the treatment of diseases caused by phytopathogenic fungi is object of this invention, which process consists of the following steps:

a) Growing and sporulating *Bacillus velezensis* strain AH2 in a suitable culture medium by means of submerged fermentation. In this step cell count values on the order of $10^9$ colony forming units per milliliter ($CFU.mL^{-1}$) are reached b) Preparing the formulation by means of adding the other components to the fermented broth with the cells.

This product has good stability and preserves cell viability, without significant losses, for at least six months, at temperatures not greater than 30° C. The antifungal and plant growth stimulating activities of the formulation have been verified for more than six months, preserving its initial properties. It has shown effectiveness in the treatment of diseases caused by different phytopathogenic fungi and for the stimulation of plant growth in its application in greenhouse assays. It has also shown effectiveness for the treatment of phytopathogenic fungi and particularly of *Botrytis cinerea* in field assays.

BRIEF DESCRIPTION OF THE DRAWINGS

The previous and other features and advantages will be more fully understood from the following detailed description of several embodiments with reference to the attached drawings, in which.

PREFERRED EMBODIMENT OF THE INVENTION

Propagation of the Strain *Bacillus velezensis* AH2

An ampoule of the preserved isolate of *Bacillus velezensis* strain AH2 was taken, seeded in PDA medium plates and incubated at 30° C. for 72 hours for its activation. An inoculum was prepared from this plate for the fermenter, a portion of the culture being taken with a loop, with which a 1000 mL Erlenmeyer flask was inoculated with 100 mL of Potato Dextrose (PD) Broth medium and incubated under stirring at 30° C. for 16 hours. After that the content of the flask was inoculated in a 3 L Braun Biotech BIOSTAT® B fermenter with PD medium, a final volume of 2 L being achieved. The fermentation was carried out for 24 hours at a stirring speed of 600 r.p.m., an aeration of 1 v.v.m. (2 L.min$^{-1}$) and a temperature of 30° C. The pH was allowed to vary freely and at the end it had a value of $\leq 5.5$. A final concentration of $2 \times 10^9$ cells.mL$^{-1}$ and approximately 80% sporulation were achieved. The specific growth rate in exponential phase ($\mu$) was 0.40 h$^{-1}$. The different phases of growth were developed for the first 14 hours of culture and then the sporulation process occurred up to 24 hours.

Once the fermentation had ended, the 2 L of fermented broth were taken and propionic, sorbic and ascorbic acids at 0.5, 0.1 and 0.2% respectively were added.

The cell viability in Nutrient Agar medium was determined for this product periodically, verifying that it maintains more than 80% viability after six months of preservation at temperatures not greater than 30° C.

All the assays on the antifungal and plant growth-stimulating capacity were carried out with the product prepared following this manufacturing scheme with very satisfactory results.

In Vitro Antagonism Assays.

These assays were performed in Petri dishes. The pathogens were cultured in PDA plates for 48-72 hours at a temperature of 25° C. A portion of approximately 1 cm in diameter was then taken, which portion was placed in the center of a plate with PDA medium. Said plate was inoculated at the ends with *Bacillus velezensis* strain AH2 by means of a loop. It was subsequently incubated for 48-72 hours at 28° C. until observing the inhibition. In the case of the assay with *Botryosphaeria* sp., it was furthermore also cultured in stirred PD medium, it was centrifuged and the supernatant was added in 1 cm$^2$ wells in the same plate to determine the antifungal capacity of the cell-free fermented broth.

Figure 1:
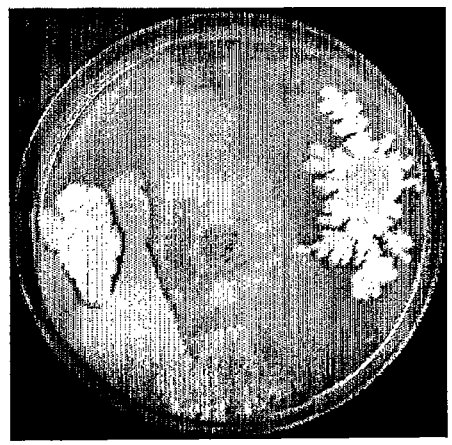
FIG. 1 shows the in vitro antagonism assays against some of the tested pathogens.
Figure 1:
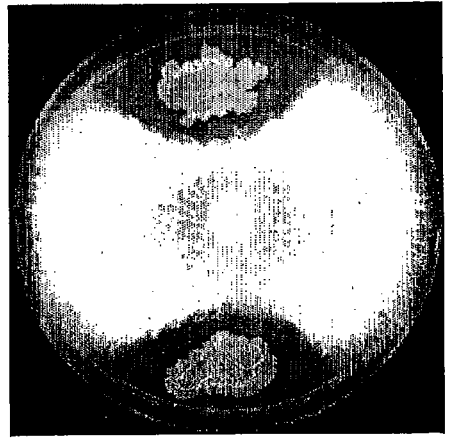
Figure 1:
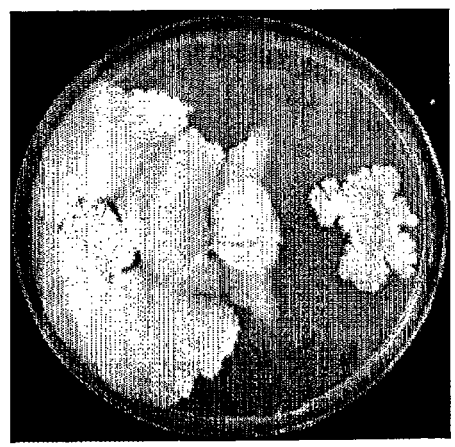
Figure 1:
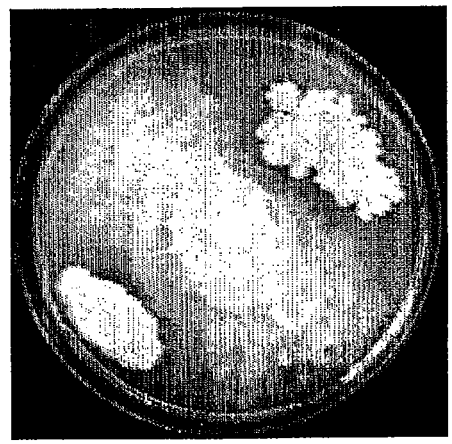
Figure 1:
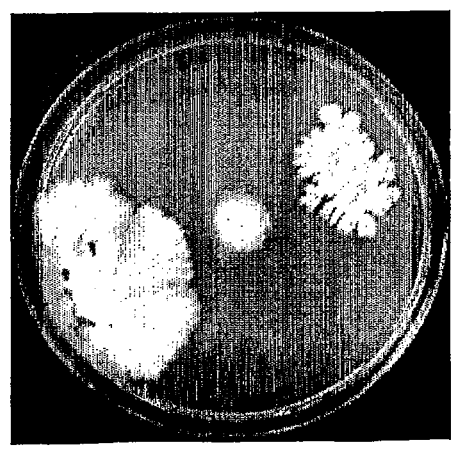
Figure 1:
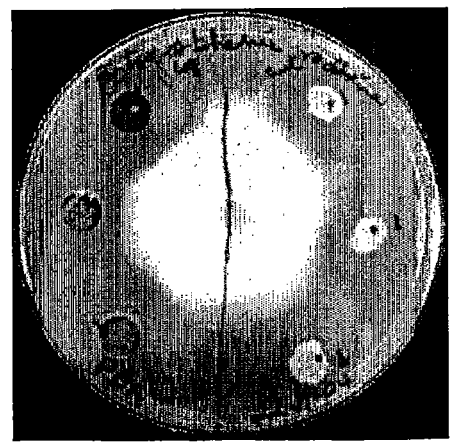

FIG. 1 shows the in vitro antagonism assays against some of the tested pathogens. As can be observed, there is a strong fungal growth inhibitory activity in each of the phytopathogenic fungi assayed.

In addition, the assay performed with the supernatant of the culture in the case of *Botryosphaeria* sp. shows that the bacterium has exocellular antifungal activity, as occurs with many other strains of the *Bacillus* genus.

Plant Growth Stimulation Assays

To verify the capacity to stimulate plant growth, an assay was carried out in cucumber plants in experimental greenhouse conditions in plant pots. The Bioprón PMC3 product from Probelte S.A. was used as a positive control given its acknowledged capacity to stimulate the plant growth of different crops.

Figure 2:
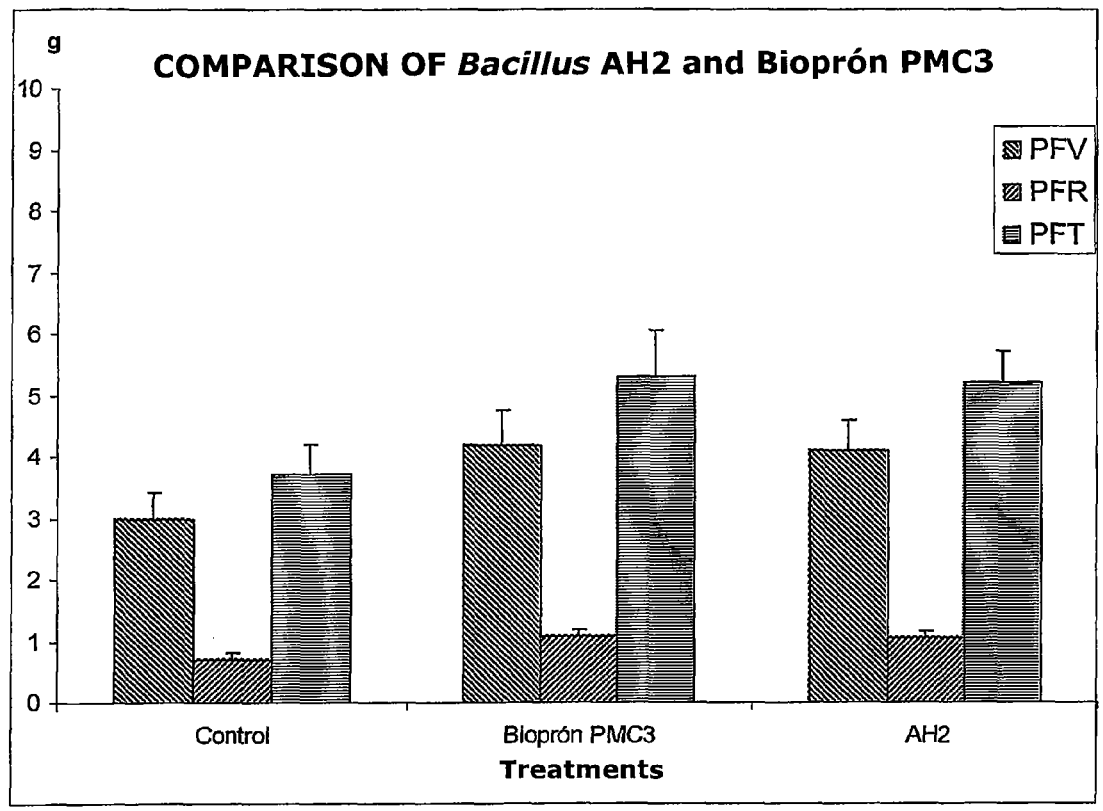
FIG. 2 is a chart illustrating results of an assay carried out in cucumber plants in experimental greenhouse conditions in plant pots.

The results of this assay are shown in FIG. 2.

As can be observed in this FIG. 2, there was a considerable increase in the Total fresh weight as well as in that of the green part and that of the root. Although these values are lower, they were not statistically different with 95% confidence from those obtained when the Bioprón PMC3 was used, whereas they were different, as observed in the graph, from the values of the control. These assays were performed in other crops such as tomato and lettuce, similar results being obtained, which allowed verifying the plant growth stimulating-capacity of *Bacillus velezensis* strain AH2 isolated in the research laboratories of Probelte S.A.

EFFICACY ASSAY IN PRODUCTION CONDITIONS

| | |
|---|---|
| Reference of the assay: | AFS Mazarron Tomato 2006 |
| Product commercial name: | AFS |
| Crop: | Amadeo Tomato (*Lycopersicon esc.* M) |
| Conditions: | Production greenhouse, localized irrigation |
| Planting pattern: | 1 m × 0.6 m |
| Planting density | Approx. 16600 plants/ha |
| Type of soil: | Loamy sand |
| Active ingredient: | *Bacillus velezensis* strain AH2, 10$^8$ CFU/mL |
| Generic use of the product: | Fungicide |
| Type of formulation: | Soluble liquid |
| Application mode: | Leaf spraying |
| Target pathogen object of the assay: | *Botrytis cinerea* |
| Reference product: | Karbel (Registered at the R.O.P.M.F. (Official registry of plant protection products and materials) No. 23506/14 (25% Carbendazime + 25% Diethofencarb. 1 g/L of Probelte S.A.) |

Thesis to be assayed

| Thesis | Name | Doses | Active ingredient or ingredients |
|---|---|---|---|
| No. 1 | CONTROL | | |
| No. 2 | AFS | 15 (mL/L.) | *Bacillus velezensis* 10$^8$ CFU/mL |
| No. 3 | TRL | 5 (mL/L) | *Trichoderma harzianum* + *T. viride* 10$^8$ CFU/mL |
| No. 4 | AFS | 5 (L/ha) | *Bacillus velezensis* 10$^8$ CFU/mL |
| No. 5 | KARBEL | 1 (g/L) | 25% Carbendazime + 25% Diethofencarb |

An assay with a completely randomized block design with four repetitions was performed. The size of the elemental plot was 15 m$^2$ and 60 m$^2$ of total area for each treatment.

Two applications were performed during the assay by means of leaf spraying, $T_1$ and $T_2$, in a broth volume of 1200 L/ha. The first application was 2.5 months after planting and the second application was 17 days after performing the first one.

To perform the evaluation of the assay, the total number of tomatoes that each plant had was counted in the elemental plot, the tomatoes with *Botrytis* were noted and a value of 1 to 4 was given depending on the intensity of the attack of the pathogen and based on this the infestation calculation was performed. Three assessments were carried out during the assay, an initial assessment $V_0$ and two assessments once the treatments had ended, $V_1$ 7 days after performing the second treatment and $V_2$ 15 days after.

Results of the Assay.

Assessment $V_0$. No symptom of the disease was observed

First assessment $V_1$ (One week after the second treatment)

| BLOCKS | A | B | C | D | Mean | Total |
|---|---|---|---|---|---|---|
| THESIS | | | Infestation | | | |
| CONTROL | 0.063 | 0.145 | 0.083 | 0.145 | 0.108 | 0.433 |
| AFS (15 mL/L) | 0 | 0.020 | 0 | 0.020 | 0.01 | 0.04 |
| TRL (5 mL/L) | 0 | 0.020 | 0.041 | 0 | 0.015 | 0.061 |
| AFS (5 L/ha) | 0.041 | 0.041 | 0.041 | 0.020 | 0.035 | 0.143 |
| KARBEL (1 g/L) | 0 | 0.041 | 0 | 0.041 | 0.020 | 0.082 |

| ABBOTT Efficacy | | |
|---|---|---|
| THESIS | MEAN | % EFFICACY |
| CONTROL | 0.108 | |
| AFS (15 mL/L) | 0.01 | 90.82 |
| TRL (5 mL/L) | 0.015 | 85.99 |
| AFS (5 L/ha) | 0.035 | 67.16 |
| KARBEL (1 g/L) | 0.020 | 81.17 |

| Duncan's multiple range test | |
|---|---|
| THESIS | Significant differences |
| CONTROL | b |
| AFS (15 mL/L) | to |
| TRL (5 mL/L) | to |
| AFS (5 L/ha) | b |
| KARBEL (1 g/L) | to |

Second Assessment $V_2$ (Fifteen Days after the Second Treatment)

| BLOCKS | A | B | C | D | Mean | Total |
|---|---|---|---|---|---|---|
| THESIS | | | Infestation | | | |
| CONTROL | 0.166 | 0.104 | 0.250 | 0.250 | 0.192 | 0.77 |
| AFS (15 mL/L) | 0 | 0.062 | 0.041 | 0.041 | 0.036 | 0.144 |
| TRL (5 mL/L) | 0 | 0.020 | 0.083 | 0.062 | 0.041 | 0.165 |
| AFS (5 L/ha) | 0.020 | 0.083 | 0.041 | 0.104 | 0.062 | 0.248 |
| KARBEL (1 g/L) | 0.020 | 0.083 | 0.041 | 0.062 | 0.051 | 0.206 |

| ABBOTT Efficacy | | |
|---|---|---|
| THESIS | MEAN | % EFFICACY |
| CONTROL | 0.192 | |
| AFS (15 mL/L) | 0.036 | 81.30 |
| TRL (5 mL/L) | 0.041 | 78.57 |
| AFS (5 L/ha) | 0.062 | 67.79 |
| KARBEL (1 g/L) | 0.051 | 73.25 |

| Duncan's multiple range test | |
|---|---|
| THESIS | Significant differences |
| CONTROL | b |
| AFS (15 mL/L) | a |
| TRL (5 mL/L) | a |
| AFS (5 L/ha) | a |
| KARBEL (1 g/L) | a |

As can be observed, in both assessments the treatment of AFS at 15 mL/L causes an protection which is effective and greater than the commercial chemical product used as s control. At all times the infestation was maintained under control and the effectiveness of the product assayed has been very high. The statistical analysis performed yielded that there are no significant differences between the assayed biological products and the control chemical product.

CONCLUSIONS

In the assay performed in Mazarron (Murcia), in leaf spraying for controlling *Botrytis cinerea* and observing the behavior thereof in the future, AFS had a very good activity respect to the control which had not received any treatment.

In assessment $V_1$ efficacies on the order of the 90% were obtained for the dose of 15 mL/L, In assessment $V_2$ the efficacies were high, over 70% and particularly, in the case of AFS over 80%.

It should be emphasized that the incidence level of the pathogen in the crop was maintained under control with the treatments performed.

Upon performing the variance analysis in both assessments, on the parameters measured, when Duncan's multiple range test was performed, it was found that there are no differences with 99% confidence between the dosages under study and there are differences with respect to the untreated control.

No toxicity symptom was observed in the crop at the highest dose.

It is therefore concluded that AFS at a dosage of 15 mL/L is a formulation suitable for the control of *Botrytis cinerea* in tomatoes.

The invention claimed is:

1. A pure culture of *Bacillus velezensis* strain AH2, CECT-7221, and mutants thereof, having antifungal activity by producing antagonist substances, having the capability of solubilizing phosphates, of producing indole-3-acetic acid and of producing siderophores, as well as growing on 1-aminocyclopropane-1-carboxylic acid (ACC) as a sole nitrogen source.

2. A product for the biological control of phytopathogenic fungi and stimulating plant growth, containing an effective amount of viable cells of a biologically pure culture of *Bacillus velezensis* strain AH2, CECT-7221.

3. A product for the biological control of phytopathogenic fungi and stimulating plant growth according to claim 2, wherein the viable cells are in the form of spores.

4. A product for the biological control of phytopathogenic fungi and stimulating plant growth according to claim 2, wherein the cells are obtained by means of a submerged fermentation process in which the spore concentration is greater than $10^9$ CFU/mL.

5. A product for the biological control of phytopathogenic fungi and stimulating plant growth according to claim 2, containing a total spore concentration greater than $10^9$ CFU/mL.

6. A product for the biological control of phytopathogenic fungi and stimulating plant growth according to claim 4, containing, in addition to the bacterial cells, the supernatant of the culture.

7. A product for the biological control of phytopathogenic fungi and stimulating plant growth according to claim 2, wherein the product is suitable for leaf spraying.

8. A product for the biological control of phytopathogenic fungi and stimulating plant growth according to claim 3, wherein the cells are obtained by means of a submerged fermentation process in which the spore concentration is greater than $10^9$ CFU/mL.

9. A product for the biological control of phytopathogenic fungi and stimulating plant growth according to claim 3, containing a total spore concentration greater than $10^9$ CFU/mL.

* * * * *

UNITED STATES PATENT AND TRADEMARK OFFICE
CERTIFICATE OF CORRECTION

PATENT NO.       : 8,404,476 B2                                         Page 1 of 1
APPLICATION NO.  : 12/531933
DATED            : March 26, 2013
INVENTOR(S)      : Fernandez Martinez et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 806 days.

Signed and Sealed this
First Day of September, 2015

Michelle K. Lee
*Director of the United States Patent and Trademark Office*